(12) United States Patent
Kanthimathi et al.

(10) Patent No.: US 7,169,191 B2
(45) Date of Patent: Jan. 30, 2007

(54) PROCESS FOR PREPARING A SYNTHETIC ALUMINIUM TANNING AGENT

(75) Inventors: Mookandi Kanthimathi, Tamil Nadu (IN); Palanisamy Thanikaivelan, Tamil Nadu (IN); Jonnalagadda Raghava Rao, Tamil Nadu (IN); Balachandran Unni Nair, Tamil Nadu (IN); Thirumalachari Ramasami, Tamil Nadu (IN)

(73) Assignee: Council of Scientific and Industrial Research, New Delhi (IN)

( * ) Notice: Subject to any disclaimer, the term of this patent is extended or adjusted under 35 U.S.C. 154(b) by 2 days.

(21) Appl. No.: 10/392,385

(22) Filed: Mar. 20, 2003

(65) Prior Publication Data

US 2004/0181881 A1  Sep. 23, 2004

(51) Int. Cl.
C08G 12/10 (2006.01)
C08G 8/04 (2006.01)

(52) U.S. Cl. .................. 8/94.21; 8/94.29; 8/94.33; 528/150; 528/230; 528/239; 528/242

(58) Field of Classification Search .............. 8/94.28, 8/94.19, 94.29, 94.21, 94.33; 556/183; 528/150, 528/230, 239, 242
See application file for complete search history.

(56) References Cited

U.S. PATENT DOCUMENTS 4,272,242 A * 6/1981 Plapper et al. ............... 8/94.18
4,723,001 A    2/1988 Schutz et al.
4,830,632 A    5/1989 Lauton
4,888,412 A * 12/1989 Ebel et al. .................. 528/230
5,342,916 A *  8/1994 Weiser et al. ............... 528/150

FOREIGN PATENT DOCUMENTS

| GB | 1554886 | 10/1979 |
| GB | 2069694 A | 8/1981 |
| GB | 20168999 A | 8/1991 |

\* cited by examiner

*Primary Examiner*—Douglas McGinty
*Assistant Examiner*—Preeti Kumar
(74) *Attorney, Agent, or Firm*—Nixon Vanderhye P.C.

(57) ABSTRACT

A novel synthetic aluminium tanning agent as an alternative for chromium based tanning salts without using formaldehyde was prepared by using aromatic polymeric matrix and aluminium (III) salts as raw materials with suitable masking agents. The preparation of the syntan consists of sulphonation of aromatic molecule, which is incorporated with a polymeric network along with ligands specially designed for the complexation of aluminium (III) salts. The complex can be used as a self-tanning agent in leather industry with fairly good filling behavior. The tanned leathers exhibit shrinkage temperature about 85° C. Due to the higher precipitation point of the product, it can be used for tanning directly after deliming thus eliminating the pickling process. This product, unlike the conventional phenol based products, does not undergo photo-oxidation thereby preventing the discoloration of the tanned leathers.

19 Claims, No Drawings

PROCESS FOR PREPARING A SYNTHETIC ALUMINIUM TANNING AGENT

FIELD OF THE INVENTION

The present invention relates to a process for the preparation of a novel synthetic aluminium tanning agent. More particularly the present invention provides a process for the preparation of a synthetic organo-aluminum tanning agent without using formaldehyde, which forms an alternative to chrome tanning material. The compound has use as a self-tanning agent for hides and skins. Additionally, it is envisaged to be capable to produce fuller leathers with adequate shrinkage temperature for producing leathers with desirable properties. It is also envisaged that the white base of the leathers enhances dyeability and ads as dye saver apart from ample production of white leathers.

BACKGROUND OF THE INVENTION

Conventionally skins/hides are stabilised against microbial degradation by tanning. Chrome tanning has been the most predominant method of tannage for the commercial purpose. The major limitation associated with this is that the chrome tanned leathers are empty in nature and hence need heavy retanning for its final performance. Unlike chamois leather, which is essentially of oil tanned, chrome tanned leather does not provide any lubrication among the fibres. Hence strong fatliquoring becomes mandatory for the desired level of softness.

Conventional chrome tanning practices employ basic chromium sulphate salt, a progenitor of several chromium species, having various charges and degree of polymerisation. The kinetic inertness of certain chromium species lends itself to poor exhaustion (50–70%) of chrome tanning salt. Thus the commercial chrome tanning activities release chromium in the range of 2000–5000 ppm.

Bellavere et al (Environmental Technology Letters, 2, 119, 1981), report that the environmental consequences arising from discharge of industrial wastewater containing chromium into water bodies are enormous. Tsou et al (Chemical Research in Toxicology, 10, 962, 1997) have proved that chromium has the ability to cause cancer, Blankenship et al (Toxicology and Applied Pharmacology, 126, 75, 1994) have reported even cell death as ultimate result due to the influence of chromium. Wide ecological concern as well as economic loss has compelled researchers to look for suitable alternatives to chromium.

Several methods have been evolved over the years for better management of chromium in leather industry, as reported by Chandrasekaran (Leather Science, 34, 91, 1987). Among them the development of mineral alternatives to chromium have been gaining momentum.

Aluminum tanning is one of the oldest methods of tanning. An old name 'tawing' has been used for this process, which consists of treating the skin with potassium alum in the form of paste including sodium chloride, egg yolk, flour and water. Aluminum tanned leathers are sensitive to water and heat. Aluminum tanned leather has a shrinkage temperature in the range of 75–82° C. depending on the method of tanning used. Its water resistance is unsatisfactory, since even a wash with the cold water slowly removes aluminium compounds from leather. Aluminium being d° element, its complexes are much less stable than those of chromium; and thus their binding to collagen is much weaker. This is the reason why aluminium salts are used in contemporary tanning almost exclusively in combined tannage to processes. Generally aluminium tanning is done in floats of zero basicity at high concentrations in the presence of sodium chloride to prevent swelling, because the pH of the float is as low as 2.5–3.5. No washing is employed after tanning.

A detailed study of the masking action of organic acids on aluminium sulfate and chloride was done by Simoncini et al (Cuoio Pelli Mat. Conc. 54, 439 & 711, 1978). They have described a tanning method based on the use of aluminium complex containing citric acid or ethylenediamine tetra acetic acid as complexing agent, which gives good results. However, the process requires a pretanning and retanning with vegetable tans and glutaraldehyde.

In a detailed study by Williams-Wynn (Journal of the Society of Leather Technologists and Chemists, 53, 64, 1969) using various ligands such as formate, acetate, lactate, tartrate and citrate, most stable leathers are obtained with formate, acetate and lactate with shrinkage temperature in the range of 74–78° C. If the complexing agent is too strong it will not be displaced by protein carboxyl groups and the skin will remain untanned. Similar conclusions have been drawn by Kuntzel and Rizk (Leder, 13, 101, 1962).

Mezey (PhD Thesis, Faculty of Science, Lyon, France, 1925) has studied the tanning effect of aluminum sulphate on unlimed skin at various basicities in the presence and absence of common salt. The absence of salt produces hard and horny translucent skin without leathery feel upon drying, which is due to swelling induced by absorption of sulphuric acid. The presence of a sufficient amount of common salt to repress the swelling effect produces supple and opaque leather. However, on washing it reverts to the swollen unlimed skin condition. Studies on tanning using previously adjusted basic solutions of aluminium sulphate by Chambard and Grail (Bull. assoc. franc. chimistes inds cuir et doc. sci. et tech. ind. cuir, 10(3), 17, 28, 1948) and Mezey (PhD Thesis, Faculty of Science, Lyon, France, 1925) have proved that the tanning using various basic aluminum sulphate solutions without common salt results in hard and horny untanned skins in spite of higher absorption of tanning bath components. In the presence of salt, opaque and supple leather having better resistance to hydrolysis than the leather, which is obtained by tannage using zero basicity and shrinkage temperature being about 65 rather than 47° C.

Aluminium based tanning agents like Lutan B and ATC-21 have not found much commercial acceptability because of the ready reversal of aluminium as aluminium hydroxide at pH values in the range of 5.0–6.0. Lipowski (U.S. Pat. No. 4,443,382, 1984) has developed an aluminium salt of aromatic sulfonic acid condensate for retanning applications. However, the polymeric matrix is made using formaldehyde. The most commercial use of aluminium in leather industry until now has been as a dye adjunct. The high cationic potential of Al(III) makes such salts useful for enhancing the color yield.

It has been reported that polyhydroxy aluminium gels aid the exhaustion of chromium during tanning and function as chrome saver by Ramsami et at (Proceedings of the 22$^{nd}$ LERIG, Madras, 167, 1987). However, the reversibility in binding to leathers has limited the usage of Al(III) salts as chrome saver. Aluraa, an aluminium based synthetic tanning agent, has aluminium in the stabilized form and binds irreversibly to the substrate as reported by Kanthimathi et al (Leather Science, 32, 59, 1985). By using this aluminium syntan as chrome saver, the exhaustion level of chromium improves to about 90% as reported by Rao et al (Proceedings of the XXV$^{th}$ ILTCS congress, Chennai, 295, 1999). However, this syntan was used only as a co-tanning agent along with 4–6% chrome salt. Further, the syntan was based on formaldehyde condensates. Swarna et al (Proceedings of the XXV$^{th}$ IULTCS Congress, Chennai 322, 1999) has reported about such formaldehyde condensates that the tanned leathers on aging may release free formaldehyde ranging from 1500 to 15000 ppm, which does not meet the tolerable limit of 5–10 ppm of free formaldehyde as accounted by Mark et al (Kirk Othmer Encyclopedia of Chemical Technology, Volume 13, John Wiley and Sons, New York; 3$^{rd}$ Edition, 1978). The tanning potency of phenol-formaldehyde condensates has been reported by Gustavson (The Chemistry of Tanning Processes, Academic press, Volume 2, p. 4, 1956). But the major disadvantages of such polymeric condensates are a) the tanned leathers show discoloration
b) the sulfonic acid groups introduced in the system to give soluble matrix would competitively inhibit the binding of anionic dyes
c) slow release of formaldehyde from the tanned leathers on aging may pose hazardous environment.

The main pre-requisite for conventional chrome tanning process, carried out using either basic chromium sulphate (BCS) or high exhaust chrome tanning salt, is to pickle the pelt by employing acid and salt in aqueous medium whereby the emanated liquor is loaded with dissolved solids, chlorides and sulphates, leading thereby to the environmental pollution.

OBJECTS OF THE INVENTION

The main objective of the invention is to provide a process for the preparation of a novel synthetic aluminium tanning agent, which obviates the drawbacks stated above.

Another objective of this invention is to provide an organo aluminium complex for direct tanning of delined pelts without the conventional pickling process thereby reducing the total dissolved solids in the effluent.

Yet another objective of the invention is to provide a method for the preparation of Al(III) ting salt in homogenous chemical formulation in which Al(III) binds irreversibly with skin/hide matrix and resists washing even at a pH 7.

Still another objective of the invention is to provide a method for the preparation of Al(III) tanning salt which when used in tanning gives leathers with shrinkage temperature more than 80° C. unlike the conventional aluminum tanned leathers.

Still another objective of the invention is to provide a product for the manufacture of white leathers through an eco-friendly application procedure.

Yet another objective of the invention is to provide a product, which serves as dye saver and efficient chrome saver.

Still another objective of the invention is to provide aluminium based syntan, which offers soft and fuller leathers unlike the conventional chrome tanned leather.

SUMMARY OF THE INVENTION

Accordingly the present invention provides a process for the preparation of a novel synthetic aluminium tanning agent, which comprises
i) sulfonating an aromatic compound having up to 14 carbon atoms followed by the addition of an aqueous mixture of organic ligands and polyfunctional polymer,
ii) adding trivalent aluminium salt along with water to the reaction mixture formed in step(i) and mixing the reaction mass to form a complex,
iii) adding sulfosalicylic acid to the reaction mixture formed in step(ii) to form a slurry,
iv) adjusting pH of the slurry formed in step (iii), in range of 2.5–3.0 by alkalinizing agent,
v) drying the slurry to obtain the tanning agent in powder form In one embodiment of the invention, the sulfonation in step (i) is carried out at a temperature in the range of 25–160° C.

In yet another embodiment of the invention, the aqueous mixture of organic ligands and polyfunctional polymer is added to the sulfonated aromatic compound at a temperature in the range of 60–80° C.

In a further embodiment of the invention, the addition of trivalent aluminium salt along with water to the reaction mixture formed in step(i) is carried out at a temperature in the range of 60–80° C.

In another embodiment of the inventions the addition of sulfosalicylic acid to the reaction mixture formed in step(ii) is done at a temperature in the range of 60–80° C.

In yet another embodiment of the invention, the slurry obtained in step (iv) is aerated for a period of 30–60 min before drying at a temperature in the range of 130–260° C. to get the tanning agent in powder form.

In another embodiment of the invention, the aromatic compound used is selected from the group consisting of phenol, phenolic acid, naphthol, naphthalene and anthracene.

In another embodiment of the invention, the amount of the aromatic compound used is in the range of 0.5–2.0 moles per mole aluminium.

In yet another embodiment of the invention, sulfonation is carried out using sulfuric acid in an amount in the range of 1–5 moles per mole of aluminium.

In yet another embodiment of the invention, the organic ligand used is selected from the group consisting of formic acid, citric acid, phthalic acid, poly carboxylic acid, oxalic acid, salicylic acid, sodium salts thereof and any mixture thereof.

In another embodiment of the invention, the amount of organic ligands used is in the range of 0.001–0.05 mole per mole of aluminium.

In yet another embodiment of the invention, the polyfunctional polymer used is selected from the group consisting of polyacrylic acid, polyacryl amide, polymethacrylic acid, and any mixture thereof.

In a further embodiment of the invention, the amount of the polyfunctional polymer used is in the range of 0.0001–0.001 mole per mole of aluminium.

In yet another embodiment of the invention, the trivalent aluminium salt is selected from the group consisting of aluminium sulfate, aluminium chloride, aluminium ammonium sulfate and aluminium potassium sulfate.

In another embodiment of the invention, the amount of water added to the reaction mixture is in the range of 5–30 moles per mole of aluminium.

In yet another embodiment of the invention, the amount of sulfosalicylic acid used is in the range of 0.001–0.01 moles per mole of aluminium.

In yet another embodiment of the invention, the amount of sulfuric acid used for sulfonating aromatic compound is in the range of 0.001–0.01 moles per mole of aluminium.

In another embodiment of the invention, drying of the slurry is done by drum drying or spray drying.

DETAILED DESCRIPTION OF THE INVENTION

The process of the present invention is described below in detail.

An aromatic hydrocarbon having up to 14 carbon atoms, calculated as 0.5–2.0 moles per mole of aluminium to be used, is sulfonated by known method using 1 to 5 moles sulphuric acid per mole of aluminium for a period of not less than 60 minutes at a temperature in the range 25–160° C. An aqueous mixture of 0.001–0.05 mole of organic ligand per mole of aluminium is then added to the sulfonated mass along with 0.0001–0.001 moles polyfunctional polymer per mole of aluminium at a temperature of 60–80° C. with continuous stirring whereby the organic matrix is built up.

Trivalent aluminium salt is then added to the resulting mixture along with 5–30 moles of water per mole of aluminium while maintaining the temperature in the range of 60–80° C. Al(III) being a $d^0$ non-transition element, needs a critical additive that is capable of converting it to a pseudo-transition element by transferring the electrons to 3 s, 3 p and 3 d orbitals. Hence, the reaction is continued for a period of 60 minutes. A critical additive in the range of 0.001–0.01 mole per mole of aluminium is sulfonated by known method using 0.01–0.01 moles sulphuric acid per mole of aluminium for a period of not less than 3 hours at a temperature in the range 25–28° C. The sulfonated critical additive is then added to the reaction mixture. The heating and stirring was continued for another 30 min. after which the completion of the reaction is conformed by known solublization technique. The resulting mixture is then adjusted to a pH of 25–3.0 by conventional method. The slurry is dried conventionally at a temperature range of 130–260° C. to obtain the organo aluminium complex as a white powder.

The novelty and non obviousness of the present development lies in using polyfunctional polymer for providing a polymeric matrix without methylene bridge with suitable critical additive that is capable of anchoring a $d^0$ non-transition element, Al(III), by charge transfer mixing of 3 s, 3 p and 3 d orbitals. The irreversible binding of aluminium to the organic matrix is achieved by using organic ligands in combination with critical additive having ligating sites capable of anchoring trivalent aluminium ion.

The invention is described in the following examples, which are provided for illustration only and should not be construed to limit the scope of the present invention

EXAMPLE 1

25 gms of naphthalene and 25 ml of conc. sulfuric acid were taken into a 250 ml round bottomed flask fitted with a stirrer. The contents of the flask were heated to 80° C. for 120 minutes with constant stirring. A drop of the resulting mass was taken in a beaker and 1 ml water was added to the same with shaking. A clear solution without any naphthalene smell was obtained confirming the completion of sulfonation. Simultaneously, 0.5 gm salicylic acid was taken in a separate beaker and 0.5 ml concentrated sulfuric acid was added with stirring at 25° C. The slurry was left aside with occasional stirring for 3 hrs. The naphthalene sulfonic acid, prepared in flask was allowed to cool down to 60° C. and transferred a reactor fitted with a thermometer, stirrer and a dropping funnel. The mass was stirred continuously for a period of 10 min. while maintaining the temperature at 60° C. with the help of the thermostat. A mixture of 0.2 gm poly acrylic acid, 0.25 gm phthalic acid, 1 gm citric acid and 0.14 gm salicylic acid was dissolved in 10 ml water in a beaker and the same was added to the reaction mass in the reactor through the dropping funnel. The mixture was heated at 65° C. for 20 min. 250 gm of aluminium sulfate was added to the above mass along with 100 ml of water with vigorous stirring. The temperature of the bath was gradually raised to 70° C. and allowed heating to continue for another 60 min. The sulfo salicylic acid which was prepared in the beaker was added to above mass and heating was continued for another 30 minutes. The mixture was transferred to a bucket and pH was raised to 2.5 by adding 60 gms sodium sulfite dissolved in 100 ml water while continuing stirring. The air was passed through the resulting solution for a period of 70 minutes. Slurry was filtered using muslin cloth of pore size 5–10μ. The filtrate was drum dried at 130° C. and the powder stored in a plastic container.

The product was used for tanning the delimed goat skins at an offer of 1.5% as $Al_2O_3$ on pelt weight. The tanned leather was left over night and the shrinkage temperature was found to be 85° C. exhibiting 80–82% exhaustion of aluminium.

EXAMPLE 2

70 gms of anthracene and 50 ml of conc. sulfuric acid were taken into a 500 ml round bottomed flask fitted with a stirrer. The contents of the flask were heated to 140° C. for one hr. with continuous stirring. 1 ml of the resulting mass was taken in a beaker and 3 ml water was added to the same beaker with shaking. It was observed to form a clear solution, confirming the completion of sulfonation. In another beaker 0.3 gms salicylic acid was sulfonated simultaneously by adding 0.3 ml conc. sulfuric acid and stirred thoroughly at 28° C. This mass was kept aside for 4 hrs with occasional stirring The anthracene sulfonic acid was cooled to 60° C. and transferred to the reactor fitted with a condenser, stirrer and a dropping funnel. The reactor was fitted into a thermostated water bath and the sulfonated mass was stirred for 10 min. at a temperature of 60° C. A mixture of 1 gm citric acid, 0.06 gm oxalic acid, 0.01 gm phthalic acid, 0.03 gm sodium formate and 0.1 gm poly acrylic acid was dissolved in 15 ml water and added to the reaction mixture keeping the temperature at 60° C. The mass was heated at 65° C. for 40 minutes, 200 gms of aluminium potassium sulfate was dissolved in 150 ml water and added to the reactor while continuing the heating and stirring. The temperature was gradually raised to 75° C. The mixture was heated for one hour. The pre made sulfo salicylic acid was added to the reaction mixture and stirred for 40 min. while maintaining the above temperature. The mixture was transferred to a bucket and the pH was adjusted to 2.5 by adding aqueous slurry of 50 gms of sodium bicarbonate and stirring continued till the effervescence stopped. The mass was filtered using a muslin cloth of pore size 5–10μ. The filtrate was spray dried at a temperature of 230° C. and the powder was stored in a plastic container The product was used for tanning the delimed goat skins at an offer of 1.5% as $Al_2O_3$ is on pelt weight. The tanned leather was left over night and the shrinkage temperature was found to be 84° C., exhibiting an uptake of 80% aluminium.

EXAMPLE 3

50 gms of phenol and 100 gms of concentrated sulfuric acid were taken into a 500 ml round bottomed flask fitted with a stirrer. The contents of the flask were heated to 120° C. for 1 hr. with continuous stirring 1 ml of the resulting mass was taken in a beaker an 3 ml of water was added. On shaking, a clear solution was obtained confirming the completion of sulfonation. Simultaneously, 0.04 gms of salicylic acid was sulfonated using 0.05 ml concentrated sulfuring acid at 26° C. The contents were stirred occasionally and left aside for 3 hrs. The phenol sulfonic acid prepared in the flask was allowed to cool down to 60° C. and transferred to the reactor fitted with a thermostat, stirrer and a dropping funnel. The mass was stirred for 10 min. at 60° C. A mixture of 0.6 gm poly acrylic acid, 0.05 gm of phthalic acid in 2 ml water was added to the reactor through the dropping funnel. The mixture was stirred for 30 min. maintaining the temperature at 60° C. 136 gms of ammonium aluminium sulfate was added to the above mass along with 100 ml water with vigorous stirring. The temperature of the bath was gradually raised to 70° C. and heating continued for 1 hr. The pre made sulfo salicylic acid was added to the reactor and the heating was continued for 1 hour.

The reaction mixture was transferred to a bucket and the pH was adjusted to 3.0 using sodium bicarbonate. The solution was filtered and dried using a spray drier at a temperature of 260° C. The dried product was packed in a plastic container.

This product was used for tanning the delimed goatskins at an offer of 1.5% as $Al_2O_3$ on pelt weight. The tanned leathers were aged for one day and the shrine temperature of the tanned leather was found to be 85° C., exhibiting 78% exhaustion of aluminium.

EXAMPLE 4

73 gms of phenolic acid and 100 gms of concentrated sulfuric acid were taken into a 500 ml round bottomed flask fitted with a stirrer. The contents of the flask were maintained at temperature of 28° C. for 1 hr. with continuous stirring. 1 ml of the resulting mass was taken in a beaker and 3 ml of water was added. On shaking, a clear solution was obtained confirming the completion of sulfonation. Simultaneously, 0.04 gms of salicylic acid was sulfonated using 0.05 ml concentrated sulfuring acid at 26° C. The contents were stirred occasionally and left aside for 3 hrs. The sulfonated phenolic acid prepared in the flask was allowed to cool down to 60° C. and transferred to the reactor fitted with a thermostat, stirrer and a dropping funnel. The mass was stirred for 10 min. at 60° C. A mixture of 0.6 gin poly acrylic acid, 0.05 gm of phthalic acid in 2 ml water was added to the reactor through the dropping funnel. The mixture was stirred for 30 min. maintaining the temperature at 60° C. 72 gms of aluminium chloride was added to the above mass along with 100 ml water with vigorous stirring. The temperature of the bath was gradually raised to 70° C. and heating continued 1 hr. The pre made sulfo salicylic acid was added to the reactor and the heating was continued for 1 hour. The reaction mixture was transferred to a bucket and the pH was adjusted to 3.0 using sodium bicarbonate. The solution was filtered and dried using a spray drier at a temperature of 260° C. The dried product was packed in a plastic container.

This product was used for tanning the delimed goatskins at an offer of 1.5% as $Al_2O_3$ on pelt weight. The tanned leathers were aged for one day and the shrinkage temperature of the tanned leather was found to be 84° C., exhibiting 78% exhaustion of aluminium.

EXAMPLE 5

76 gms of naphthol and 100 gms of concentrated sulfuric acid were taken into a 500 ml round bottomed flask fitted with a stirrer. The contents of the flask were heated to 70° C. for 1 hr. with continuous stirring. 1 ml of the resulting mass was taken in a beaker and 3 ml of water was added. On shaking, a clear solution was obtained confirming the completion of sulfonation. Simultaneously, 0.04 gms of salicylic acid was sulfonated using 0.05 ml concentrated sulfuring acid at 26° C. The contents were stirred occasionally and left aside for 3 hrs. The naphthol sulfonic acid prepared in the flask was allowed to cool down to 60° C. and transferred to the reactor fitted with a thermostat, stirrer and a dropping funnel. The mass was stirred for 10 min. at 60° C. A mixture of 0.6 gm poly acrylic acid, 0.05 gm of phthalic acid in 2 ml water was added to the reactor through the dropping funnel. The mixture was stirred for 30 min, maintaining the temperature at 60° C. 136 gms of ammonium aluminium sulfate was added to the above mass along with 100 ml water with vigorous stirring. The temperature of the bath was gradually raised to 70° C. and heating continued for 1 hr. The pre made sulfo salicylic acid was added to the reactor and the heating was continued for 1 hour. The reaction mixture was transferred to a bucket and the pH was adjusted to 3.0 using sodium bicarbonate. The solution was filtered and dried using a spray drier at a temperature of 260° C. The dried product was packed in a plastic container.

This product was used for tanning the delimed goatskins at an offer of 15% as $Al_2O_3$ on pelt weight. The tanned leathers were aged for one day and the shrinkage temperature of the tanned leather was found to be 85° C., exhibiting 80% exhaustion of aluminium.

The following are the advantages of the present invention:

1. Cheaper and indigenously available raw materials are used for the process of the present invention ensuring its cost effectiveness.
2. Condensation step is not required and therefore complicated control measures are not required.
3. The resulting product is pure white powder, freely soluble in water ensuring its potential use as a tanning agent.
4. The process ensures the metal ion in complex form as it resists hydrolysis up to a pH in the range of 5.5–7.0.
5. Syntan moiety is a polymeric matrix, which is built up without the use of formaldehyde, ensuring that the process of the present invention results in an eco-friendly product.
6. The product of the present invention contains 10–12% $Al_2O_3$ and has application as a self tanning agent for delimed pelts, apart from serving as dye saver and chrome exhaust aid.
7. The product produces white and soft leathers.
8. The product can be used as self-tanning agent, co-tanning agent along with BCS to improve chromium exhaustion and as retanning agent.
9. The shelf life of the product is about 1.5–2 years
10. Since the product has aluminium as cation with high positive charge, it can also be used as dye saver in post tanning.
11. Since the product does not contain any active methylene groups in the organic matrix, does not undergo photo oxidation and hence the tanned leathers do not show any discoloration on aging.

We claim:

1. A process for the preparation of a novel synthetic aluminium tanning agent, the process consisting of:
   i) sulfonating an aromatic compound having up to 14 carbon atoms followed by the addition of an aqueous mixture of organic ligands and polyfunctional polymer,
   ii) adding trivalent aluminium salt along with water to the reaction mixture formed in step (i) and mixing the reaction mass to form a complex,
   iii) adding sulfosalicylic acid to the reaction mixture formed in step (ii) to form a slurry,
   iv) adjusting pH of the slurry formed in step (iii), in the range of 2.5–3.0 by an alkalinizing agent, and optionally, subsequently aerating the slurry for a period of 30–60 minutes,
   v) drying the slurry to obtain the tanning agent in powder form and wherein the use of a polymeric matrix consisting of sulfonated aromatic hydrocarbon, organic ligands, polyfunctional polymer and sulfosalicylic acid anchors the aluminium by charge transfer of 3 s, 3 p and 3 d orbitals.

2. A process as in claim 1 wherein the sulfonation in step (i) is carried out at a temperature in the range of 25–160° C.

3. A process as in claim 1 wherein the aqueous mixture of organic ligands and polyfunctional polymer is added to the sulfonated aromatic compound at a temperature in the range of 60–80° C.

4. A process as in claim 1 wherein the addition of trivalent aluminium salt along with water to the reaction mixture formed in step (i) is carried out at a temperature in the range of 60–80° C.

5. A process as in claim 1 wherein the addition of sulfosalicylic acid to the reaction mixture formed in step (iii) is done at a temperature in the range of 60–80° C.

6. A process as in claim 1 wherein the drying in step (v) is carried out at a temperature in the range of 130–260° C. to get the tanning agent in powder form.

7. A process as in claim 1 wherein the aromatic compound used is selected from the group consisting of phenol, phenolic acid, naphthol, naphthalene and anthracene.

8. A process as in claim 1 wherein the amount of the aromatic compound used is in the range of 0.5–2.0 moles per mole aluminium.

9. A process as in claim 1 wherein sulfonation is carried out using sulfuric acid in an amount in the range of 1–5 moles per mole of aluminium.

10. A process as in claim 1 wherein the organic ligand used is selected from the group consisting of formic acid, citric acid, phthalic acid, polycarboxylic acid, oxalic acid, salicylic acid, sodium salts thereof and any mixture thereof.

11. A process as in claim 1 wherein the amount of organic ligands used is in the range of 0.001–0.05 mole per mole of aluminium.

12. A process as in claim 1 wherein the polyfunctional polymer used is selected from the group consisting of polyacrylic acid, polyacryl amide, polymethacrylic acid, and any mixture thereof.

13. A process as in claim 1 wherein the amount of the polyfunctional polymer used is in the range of 0.0001–0.001 mole per mole of aluminium.

14. A process as in claim 1 wherein the trivalent aluminium salt is selected from the group consisting of aluminium sulfate, aluminium chloride, aluminium ammonium sulfate and aluminium potassium sulfate.

15. A process as in claim 1 wherein the amount of water added to the reaction mixture is in the range of 5–30 moles per mole of aluminium.

16. A process as in claim 1 wherein the amount of sulfosalicylic acid used is in the range of 0.001–0.01 moles per mole of aluminium.

17. A process as in claim 1 wherein the amount of sulfosalicylic acid used for sulfonating aromatic compound is in the range of 0.001–0.01 moles per mole of aluminium.

18. A process as in claim 1 wherein the drying of the slurry is done by drum drying or spray drying.

19. A process as in claim 1 wherein the alkalinizing agent used in step (iv) is selected from the group consisting of sodium bicarbonate, sodium sulphite and NaOH.

* * * * *